US006840904B2

(12) United States Patent
Goldberg

(10) Patent No.: US 6,840,904 B2
(45) Date of Patent: Jan. 11, 2005

(54) MEDICAL MONITORING DEVICE AND SYSTEM

(76) Inventor: Jason Goldberg, 8 Northbank Ct., Thronhill, Ontario (CA), L3T 7J7

( * ) Notice: Subject to any disclaimer, the term of this patent is extended or adjusted under 35 U.S.C. 154(b) by 148 days.

(21) Appl. No.: 09/975,097

(22) Filed: Oct. 11, 2001

(65) Prior Publication Data

US 2003/0073884 A1 Apr. 17, 2003

(51) Int. Cl.[7] .................................................. A61B 5/00
(52) U.S. Cl. ........................ 600/300; 128/903; 128/920
(58) Field of Search ................................ 600/300–301, 600/309, 316, 322, 365, 347, 481, 484, 500, 529, 538, 587; 128/903–904, 920–925, 905; 340/573.1; 702/19; 705/2–4; 452/8–9

(56) References Cited

U.S. PATENT DOCUMENTS 4,731,726 A 3/1988 Allen, III
5,307,263 A 4/1994 Brown
5,390,238 A 2/1995 Kirk et al.
5,576,952 A 11/1996 Stutman et al.
5,701,904 A 12/1997 Simmons et al.
5,704,366 A 1/1998 Tacklind et al.
5,713,350 A 2/1998 Yokota et al.
5,772,586 A * 6/1998 Heinonen et al. ........... 600/300
5,822,715 A 10/1998 Worthington et al.
5,827,180 A 10/1998 Goodman
5,840,020 A 11/1998 Heinonen et al.
5,897,493 A 4/1999 Brown
5,899,855 A 5/1999 Brown
5,956,501 A 9/1999 Brown
5,960,403 A 9/1999 Brown
6,024,699 A * 2/2000 Surwit et al. ............... 600/300
6,047,203 A 4/2000 Sackner et al.
6,050,940 A 4/2000 Braun et al.
6,072,396 A 6/2000 Gauekl
6,168,563 B1 * 1/2001 Brown ....................... 600/301
6,175,752 B1 1/2001 Say et al.
6,221,010 B1 4/2001 Lucas (List continued on next page.)

FOREIGN PATENT DOCUMENTS

WO WO 01/65810 9/2001
WO WO 01/97703 A2 12/2001

OTHER PUBLICATIONS

Hardesty, "Clothed in Health," *Technology Review*, Jul./Aug. 2001, p. 34.

(List continued on next page.)

*Primary Examiner*—Mary Beth Jones
*Assistant Examiner*—Michael Astorino
(74) *Attorney, Agent, or Firm*—Brown Raysman Millstein Felder & Steiner LLP

(57) ABSTRACT

A portable device that receives data provided by one or more sensors and displays statistical data related to the sensor data or otherwise related to the person. Statistical data may include high, low, average, mean value, median value, standard deviation, least square, variance, distribution, compilation, etc. for or at any given time or period of time for the person being monitored, as well as for such values for segments or groups of the population, or limit values, or target values, etc. The values may represent measurements and other data related to physiological signs and parameters such as blood pressure, heart rate, body temperature, electrocardiogram, glucose level, substances and/or chemical presence or level, analyze measurements, etc. The portable device may also display such measurements. The portable device may compute the statistical data, with or without the aid of a remote computer, and/or store statistical data, and/or a remote computer may compute and/or store statistical data. The portable device may communicate with a remote computer through a wireless link from the portable device, which may compute and/or store statistical data and measurements.

10 Claims, 9 Drawing Sheets

101a Portable Device
110 Communications Unit
202 Paging Network Transmitting/Receiving Towers
204 Paging Terminal
206 Paging Network Gateway
300a Internet
310 Third Party Devices
302a WWW Server

U.S. PATENT DOCUMENTS

| | | | |
|---|---|---|---|
| 6,246,992 | B1 | 6/2001 | Brown |
| 6,375,614 | B1 | 4/2002 | Braun et al. |
| 6,402,691 | B1 | 6/2002 | Peddicord et al. |
| 2002/0133377 | A1 | 9/2002 | Brown |

OTHER PUBLICATIONS http://www.kivalo.com printed Oct. 10, 2001.

http://www.kivalo.com/process.html printed Oct. 10, 2001.

http://www.digitalangel.net/da/ printed Oct. 10, 2001 (3 pgs).

http://www.digitalangel.net/da/tech.htm printed Oct. 10, 2001 (4 pgs).

http://www.uic.edu/hsc/acad/intmed/cardio/monitor printed Oct. 10, 2001.

http://www.protocol.com/products/wireless/flexnet.asp printed Oct. 10, 2001 (2 pgs).

http://www.thinkmobile.com/news/00/39/23/ printed Oct. 10, 2001 (3 pgs).

http://www.hommed.com/patients_familites/central_station_print.html printed Oct. 10, 2001.

http://www.cardionet.com/ printed Oct. 10, 2001.

http://www.bosmedtech.com/ printed Oct. 10, 2001 (2 pgs).

* cited by examiner

Figure 6a

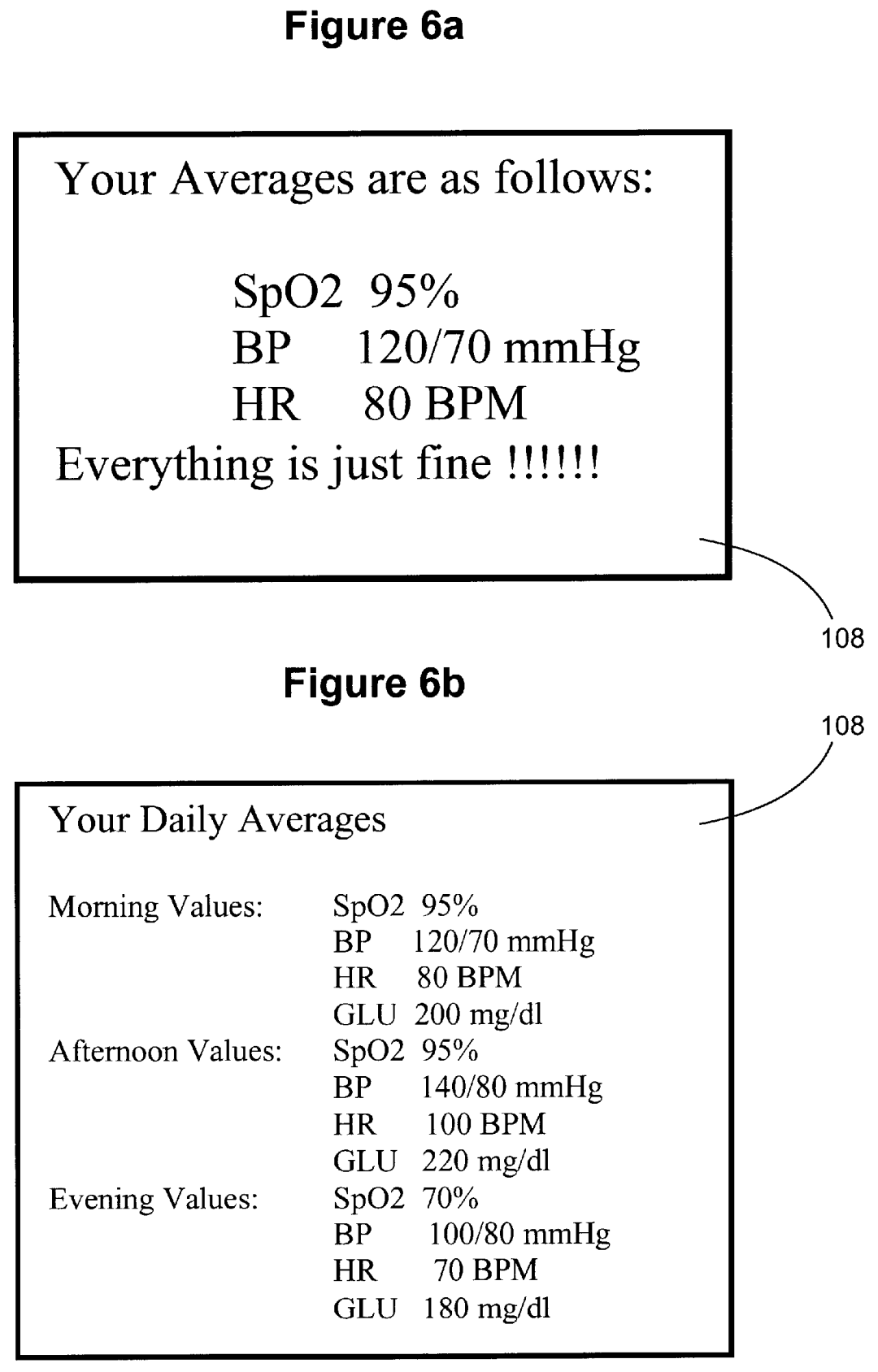

Your Averages are as follows:

SpO2 95%
BP 120/70 mmHg
HR 80 BPM

Everything is just fine !!!!!!

Your Daily Averages

| | |
|---|---|
| Morning Values: | SpO2 95% |
| | BP 120/70 mmHg |
| | HR 80 BPM |
| | GLU 200 mg/dl |
| Afternoon Values: | SpO2 95% |
| | BP 140/80 mmHg |
| | HR 100 BPM |
| | GLU 220 mg/dl |
| Evening Values: | SpO2 70% |
| | BP 100/80 mmHg |
| | HR 70 BPM |
| | GLU 180 mg/dl |

Your Weekly Averages

| | | |
|---|---|---|
| Morning Values: | SpO2 | 95% |
| | BP | 120/70 mmHg |
| | HR | 80 BPM |
| | GLU | 200 mg/dl |
| Afternoon Values: | SpO2 | 95% |
| | BP | 140/80 mmHg |
| | HR | 100 BPM |
| | GLU | 220 mg/dl |
| Evening Values: | SpO2 | 70% |
| | BP | 100/80 mmHg |
| | HR | 70 BPM |
| | GLU | 180 mg/dl |

108

108

MEDICAL MONITORING DEVICE AND SYSTEM

BACKGROUND OF THE INVENTION

The present invention relates generally to a portable medical monitoring device that is sized to be carried by a monitored person, and more particularly, to a portable device that receives data provided by one or more sensors and displays statistical data related to the sensor data. The portable device also provides measurement readings of physiological signs and parameters such as blood pressure. The portable device may operate in a system including a remote computer and a wireless communication link to the portable device. Statistical data may be computed by the portable device, with or without the aid of a remote computer, and/or provided to the portable device partially or entirely by the remote computer.

The following United States patents disclose various devices that provide health-related information based upon data obtained by or stored in the devices: U.S. Pat. No. 6,175,752 (Say et al.); U.S. Pat. No. 5,822,715 (Worthington et al.); U.S. Pat. No. 5,840,020 (Heinonen et al.); U.S. Pat. No. 5,576,952 (Stutman et al.); U.S. Pat. No. 6,047,203 (Sackner et al.).

SUMMARY OF THE INVENTION

The present invention provides a portable device that receives data provided by one or more sensors and displays statistical data related to the sensor data or otherwise to the person. Statistical data may include high, low, average, mean value, median value, standard deviation, least square, variance, distribution, compilation, etc. for or at any given time or period of time for the person being monitored, as well as for such values for segments or groups of the population, or limit values, or target values, etc. The values may represent or be related to measurements, and other data for or related to physiological signs and parameters such as blood pressure, heart rate, body temperature, electrocardiogram, glucose level, substances and/or chemical presence or level, analyze measurements, etc. The portable device may also display such measurements and/or sensor data.

The portable device may compute statistical data, with or without the aid of a remote computer, which communicates with the portable device, and/or store statistical data with or without a remote computer, which communicates with the portable device. The portable device may also compute measurements, with or without the aid of a remote computer and/or store measurements. The remote computer, if any, may also compute and/or store measurements. The portable device may communicate with a remote computer through a wireless link from the portable device.

The portable device has memory for at least temporary storage of sensor data and/or statistical data and/or measurements. The remote computer may process sensor data and provide measurements and/or statistical data, and/or the remote computer may store data and/or measurements data for transmission to a computer or portable device (e.g., of a person being monitored or a health care professional), such data and measurements being provided partially or entirely by the portable device and/or the remote computer or another device.

A remote computer has memory for at least temporary storage of data and/or measurements, and the remote computer may process sensor data and/or measurements provided by the portable device and provide statistical data and/or measurements.

In a network embodiment, the remote computer may comprise a server that can be accessed in push and/or pull modes by, for example, authorized client computers of parties such as the monitored person and his or her family members, and health care professionals. The remote computer may also initiate messages to portable devices of patients being monitored and/or computers or other electronic devices (computers, facsimile machines, PDA devices, telephone, etc.) of designated authorized parties. For example, such messages may be alerts that sensor data, measurements and/or statistical data is indicative of a medically or statistically unsatisfactory condition of the monitored person.

The invention, according to one embodiment, provides a portable medical monitoring device sized to be carried by a person to be monitored, comprising: an electronic controller; at least one memory coupled to the electronic controller that at least temporarily stores (a) sensor data provided by at least one sensor associated with the monitored person in response to at least one physiological characteristic of the monitored person, and (b) statistical data related to sensor data provided by the at least one sensor; and a display device that displays at least statistical data stored in the at least one memory.

In addition to displaying statistical data, the display device may also display sensor data and/or measurements obtained by or provided to the portable device.

The controller may include means for computing statistical data, and/or the statistical data may be provided to the device from an external source.

The statistical data may comprise at least one of high, low average, means value, median value, standard deviation, least square, variance, distribution, data, etc. The display device can display statistical data as text, graphics, or both.

In a preferred embodiment, the portable device includes a communications unit that transmits sensor data and/or measurements over a wireless communications link and receives over the wireless link at least statistical data related to sensor data or otherwise to the person being monitored. The statistical data received by the communications unit is stored at least temporarily in the at least one memory. In the preferred embodiment, the communications unit comprises a two-way pager, or any suitable wireless technology.

The invention also provides a system comprising one or more portable devices described above and a remote computer and associated memory that at least temporarily stores sensor data, measurements and/or statistical data related to the stored sensor data or otherwise to a person being monitored. In the system, the communications unit of the portable device transmits at least sensor data and/or measurements for receipt by the computer and receives at least statistical data provided by the computer.

The remote computer may comprise a web server connected to the Internet, or an intranet or other network.

The remote computer may include means for automatically providing at least sensor data, measurement data and/or statistical to one or more portable devices in accordance with an authorization procedure.

In one embodiment, the remote computer provides all statistical data stored in a portable device's memory, and in other embodiments, the electronic controller may provide statistical data stored in the portable device's memory.

The controller is preferably programmed to control transmission at least of sensor and/or measurements data by the communication unit to the remote computer in response to a user input to the portable device and to request at least statistical data and/or measurements from the remote computer in response to a user input to the device, and also to preferably control obtaining sensor data or taking a measurement in response to user input. For example, a user may initiate display of sensor data, and/or a measurement, and/or statistical data.

The remote computer may be programmed to provide statistical data to the portable device according to programmed parameters, either exclusively or in addition to user input.

In addition, the portable device can compute measurements, provide measurements to a remote computer and receive measurements stored in or computed by a remote computer.

In a preferred embodiment, the remote computer comprises a World Wide Web server. The storage of sensor, measurement and/or statistical data on the web server facilitates efficient access to such information by authorized parties. This feature can be particularly advantageous to health care professionals who can obtain and/or provide information associated with many portable devices and many monitored persons.

The server (or a remote computer), accessible by authorized parties, may transmit an automatic message alert to an authorized party communications device dependent on at least one of sensor data, a measurement and statistical data. In some embodiments, the server or remote computer comprises a value range associated with a physiological characteristic and where at least one of sensor data, measurement and statistical data is compared against the value range to determine if the automatic message alert should be transmitted. Further, the value range may be ascertained by the programmed input of a parameter associated with a physical trait of a specified monitored person into a function.

Embodiments employing processing of sensor data, and/or measurements, and/or storage of statistical data by a remote computer reduce the requirements for on-board processing and storage in a portable monitoring device.

Wireless links to the portable device may be provided by any suitable means, including pager, cell phone and mobile radio technology and systems.

BRIEF DESCRIPTION OF THE DRAWINGS

The invention may be better ascertained by referring to the following description in conjunction with the accompanying drawings, which are exemplary and not intended to be exhaustive, and in which:

FIGS. 6*a*, 6*b*, and 6*c* are illustrations of text displayed by the display of a portable medical monitoring device incorporating the invention;

FIG. 6*d* is an illustration of a graphical display displayed on the display device of a portable monitoring device incorporating to the invention.

DETAILED DESCRIPTION OF THE PREFERRED EMBODIMENT

Figure 1:
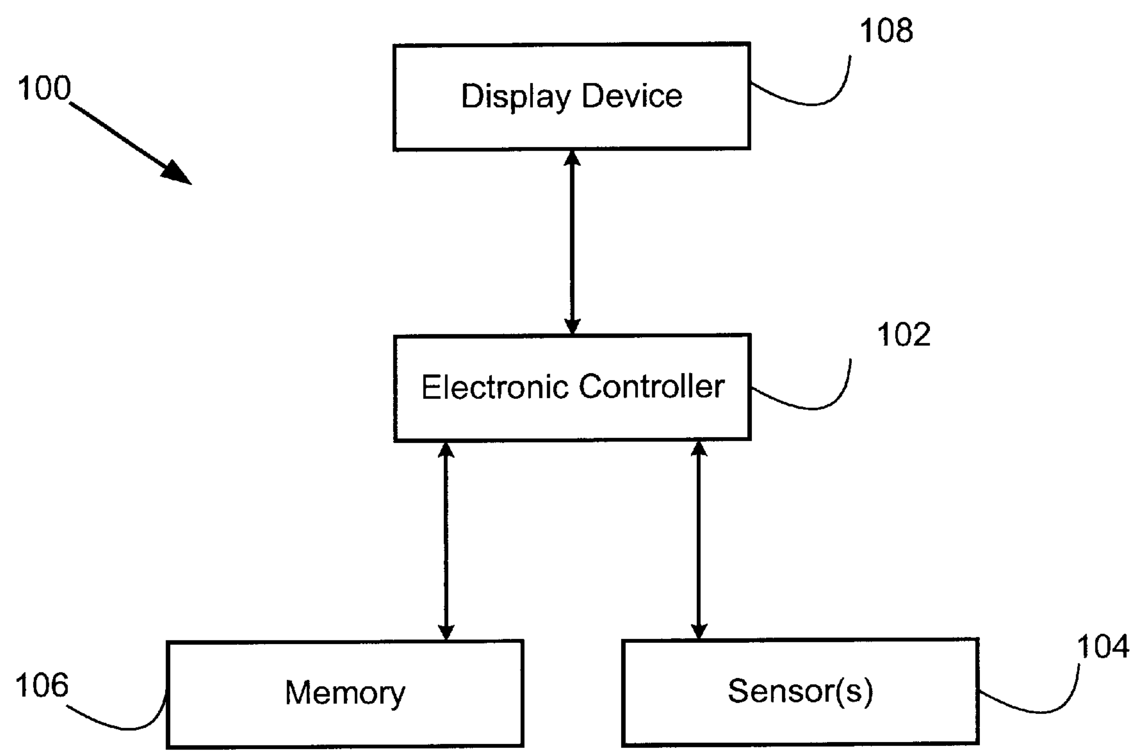
FIG. 1 is a block diagram of one embodiment of a portable medical monitoring device incorporating the invention.

Referring to FIG. 1, the portable medical monitoring device 100 according to the invention comprises an electronic controller 102, a display device 108, an electronic memory 106, and one or more sensors 104. The electronic controller can be implemented by any suitable commercially available integrated circuit application specific integrated circuit (ASIC). The sensor(s) 104 convert physiological characteristics of the monitored person into electrical signals that are provided to the electronic controller 102 or to the memory 106, where they are stored temporarily or longer term. Various sensors 104 are known in the art for converting physiological characteristics of the type disclosed herein into electrical signals, and for providing the signals to the controller 102 and/or memory 106. The sensor(s) 104 can be coupled to the controller 102 and/or memory by wire or wirelessly, and such ways of coupling are well known in the art.

In the preferred embodiment, the display device 108 is capable of displaying sensor data, and measurement data and statistical provided by the controller 102 and/or memory 106. In the embodiment shown in FIG. 1, the controller 102 processes sensor data to provide measurement data and/or statistical data. Alternatively, means can be provided for up loading and down loading data from and to device 100, and such means are well known in the art including wired and wireless, communication links, 232 communications port, serial port, etc.

Figure 1A:
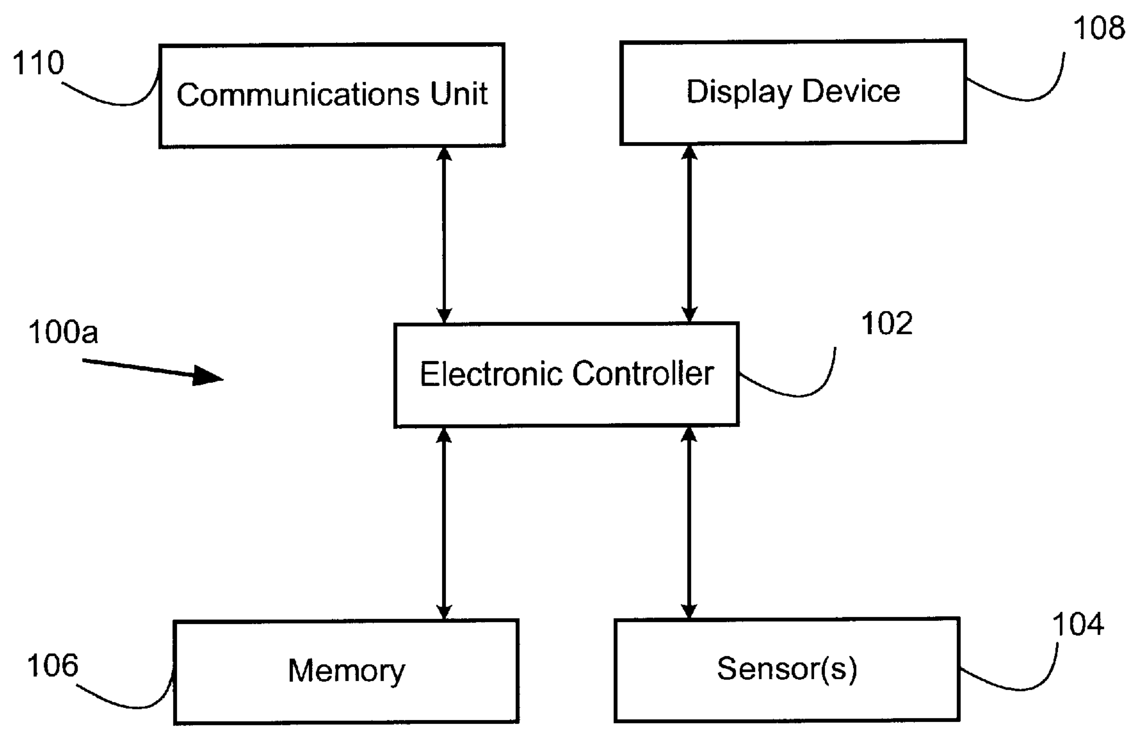
FIG. 1A is a block diagram of another embodiment of a portable medical monitoring device incorporating the invention.

FIG. 1A depicts an embodiment of a medical monitoring device 100*a* that includes a communications unit 110 for receiving and transmitting data. Sensor data, measurement and/or statistical data are provided to the communications unit 110, under control of controller 102, for transmission to a remote computer or device (not shown in FIG. 1A). The communications unit 110 may be any suitable wireless communications device, e.g., two-way wireless data pager, cell phone, two way radio, etc.

The sensors 104 are positioned as to sense physiological characteristics of the monitored person, and in the preferred embodiment, a sensor 104 can be associated with one or more of the monitored person's blood pressure, pulse, oxygen-haemoglobin saturation, glucose, body temperature, respiration, and electrolyte. As mentioned, these sensors are well know in the art and are commercially available.

Figure 2:
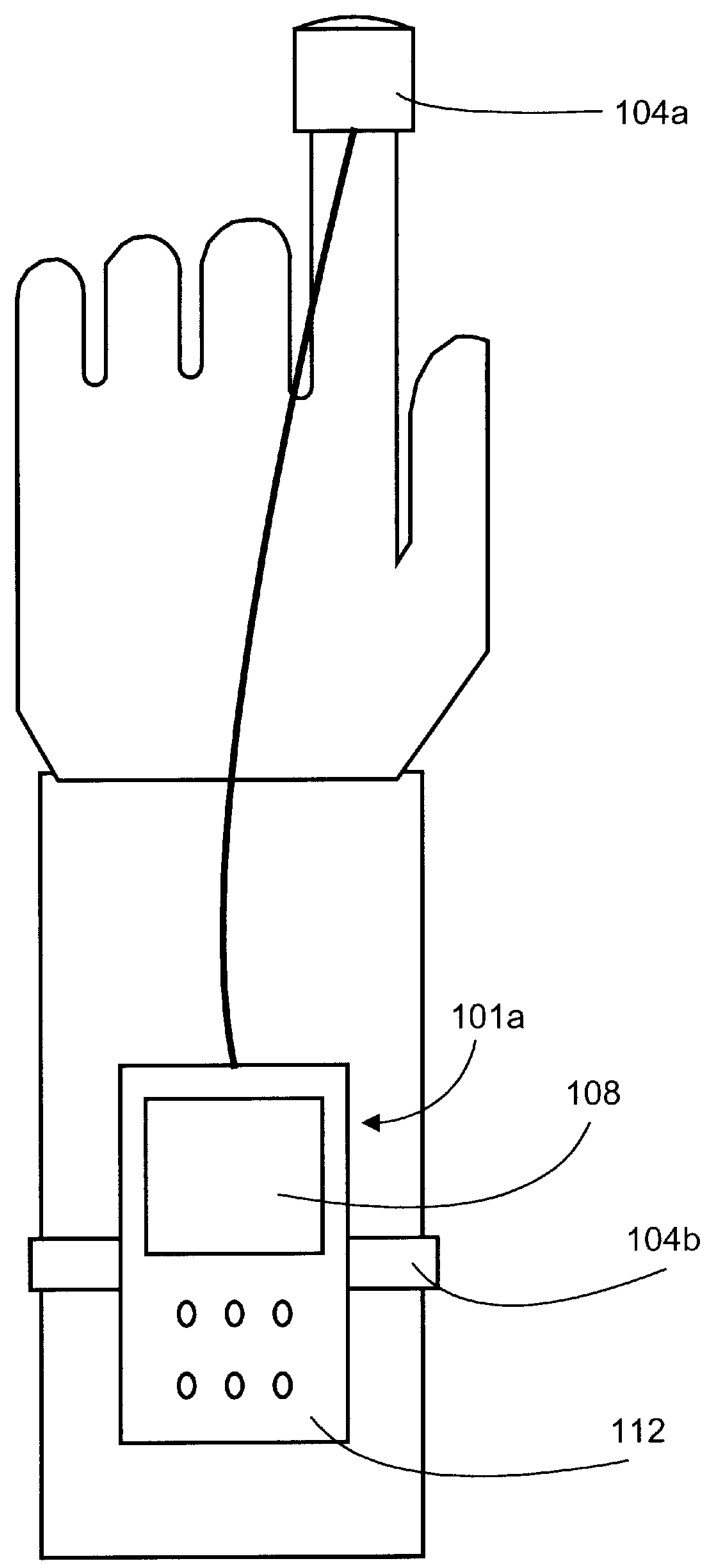
FIG. 2 is a diagram illustrating a portable medical monitoring device and sensors coupled to the device.

FIG. 2 depicts a portable device 100*a* mounted in an assembly or housing 112 that is sized to be carried by an individual, and in this embodiment, strapped to the persons wrist or forearm by any conventional strap apparatus. FIG. 2 also depicts somewhat schematically a sensor 104*a* positioned on a finger of the monitored person. Sensor 104*a* in this embodiment is a pulse oximetry sensor 104*a* to sense the monitored person's oxygen-haemoglobin saturation. In addition, a blood pressure cuff sensor 104*b* is used to sense the monitored person's blood pressure and strap also functions to the device 101*a* to a person's forearm or wrist. In another embodiment, a non-invasive sensor is used to measure electrolyte levels by emitting an electric current to sense $Na^{+1}$ and/or $K^{+1}$ ions. It is contemplated that the medical monitoring device may contain one, all, or any combination of the above-mentioned sensor types, as well as other sensors. It should be further appreciated that present invention may be comprised of any type of physiological sensor 104 suitable or use with a portable monitoring device.

Figure 3:
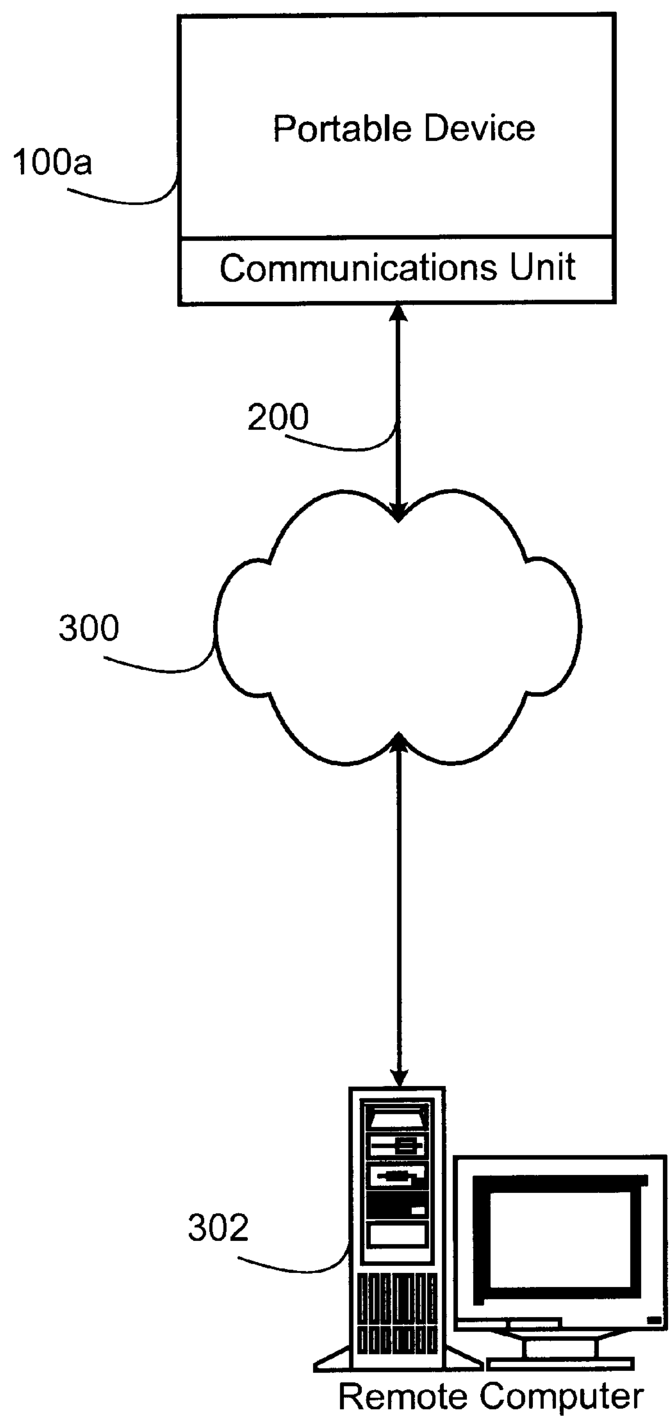
FIG. 3 is a diagram showing the communication signal path between a portable medical monitoring device and a remote computer according to one embodiment of the invention.

FIG. 3 depicts the communication signal path between the medical portable device 100*a* and a remote computer 302 through a communications network 300. The sensor data and/or measurements originating with the portable device 100*a*, are converted and transmitted by the communications unit 110, and travel through an at least partially wireless path 200 to the communications network 300. Specifically, sensor data, measurement data and/or statistical data is directed to the remote computer 302 for processing and/or storage. For example, sensor and measurement data can be processed into statistical data. Also, statistical data can be further processed and/or stored, and sensor and measurement data can be stored. Statistical information (as well as stored measurement and sensor data) is transmitted from the remote computer 302 to the portable device 100*a* in reverse fashion.

Figure 4:
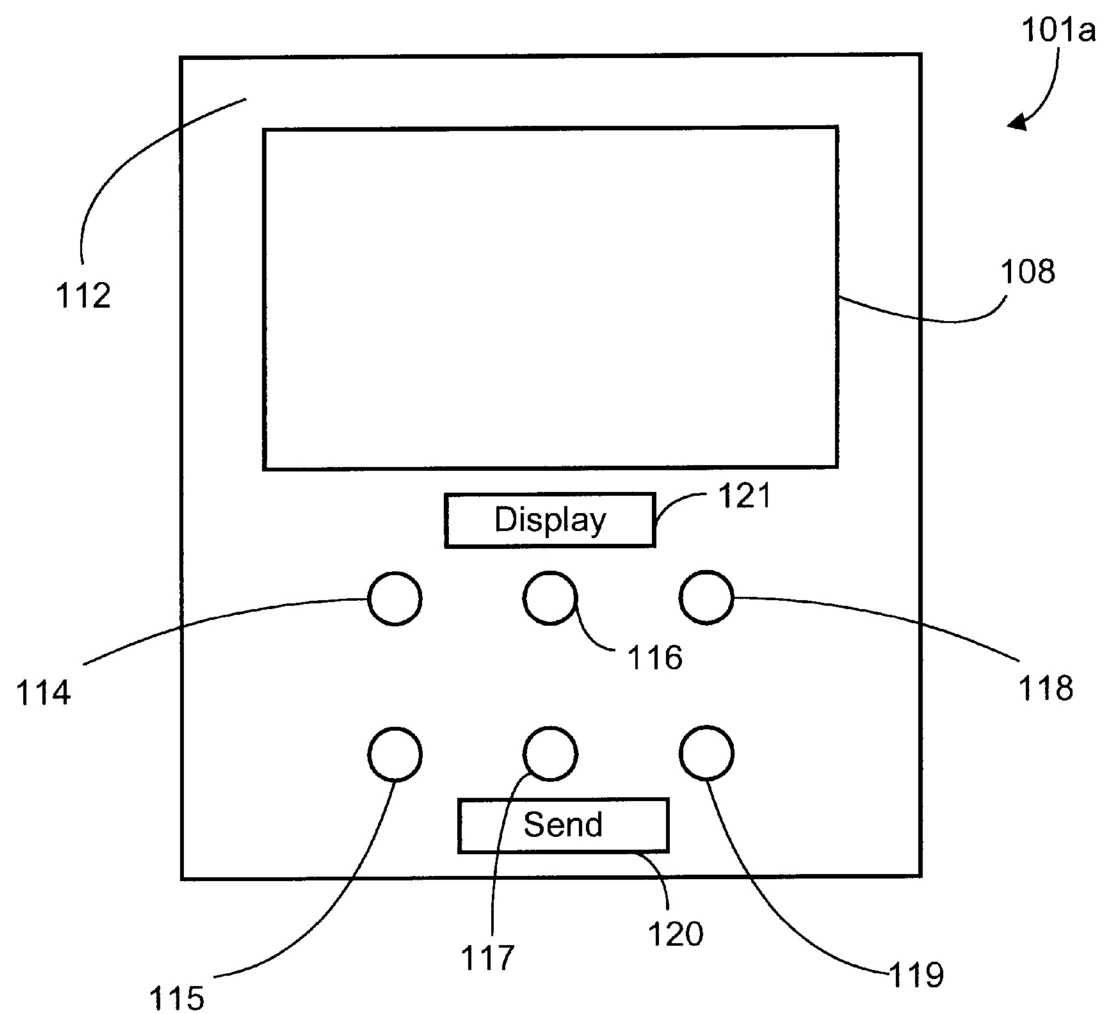
FIG. 4 is a schematic diagram illustrating a portable medical monitoring device incorporating the invention showing user-actuable switch buttons thereof.

FIG. 4 illustrates schematically a portable device 101*a* with user-actionable buttons 114–118. In the preferred embodiment, the transmission of sensor data and/or measurement data from the portable device 101*a* to the remote computer 302 can be initiated by a user actionable send button 120, thereby allowing a monitored person to send data and measurements to the remote computer 302 at the monitored person's discretion. In an alternative embodiment, the electronic controller 102 is programmed to transmit and/or request data at predetermined time intervals (i.e. twice per day).

The portable device 101*a* also has user-actuable buttons for initiating the electronic controller to direct a sensor 104 to take a measurement. A first measurement initiating button 114 is associated with a first sensor, the pulse oximetry sensor 104*a* for example, and a second measurement initiating button 115 is associated with a second sensor, the blood pressure cuff sensor 104*b* for example. Sensor data is stored in the memory 106, and is transmitted as described above to the remote computer 302 in response to the send button 120, or in an alternative embodiment, at a programmed time. A display choice user-actionable button 121 operates in cooperation with switch buttons 114–118 to display data, in both graphical and textual. Use of the display button 121 directs the electronic controller 102 to display varying statistical, sensor, and/or measurement data from the memory 106 on the display device 108 in accordance with a drop-down menu, or any other suitable user interface.

The portable device may also include in one embodiment an integrated content retrieval function for the display of content information related to, for example, news, sports, or entertainment on the display device 108. FIG. 4 illustrates a user-actionable content retrieval button 119 for initiating content retrieval. Upon receiving a content request, remote computer 302 transmits stored or retrieved content information back to the portable device 101*a*.

Figure 5:
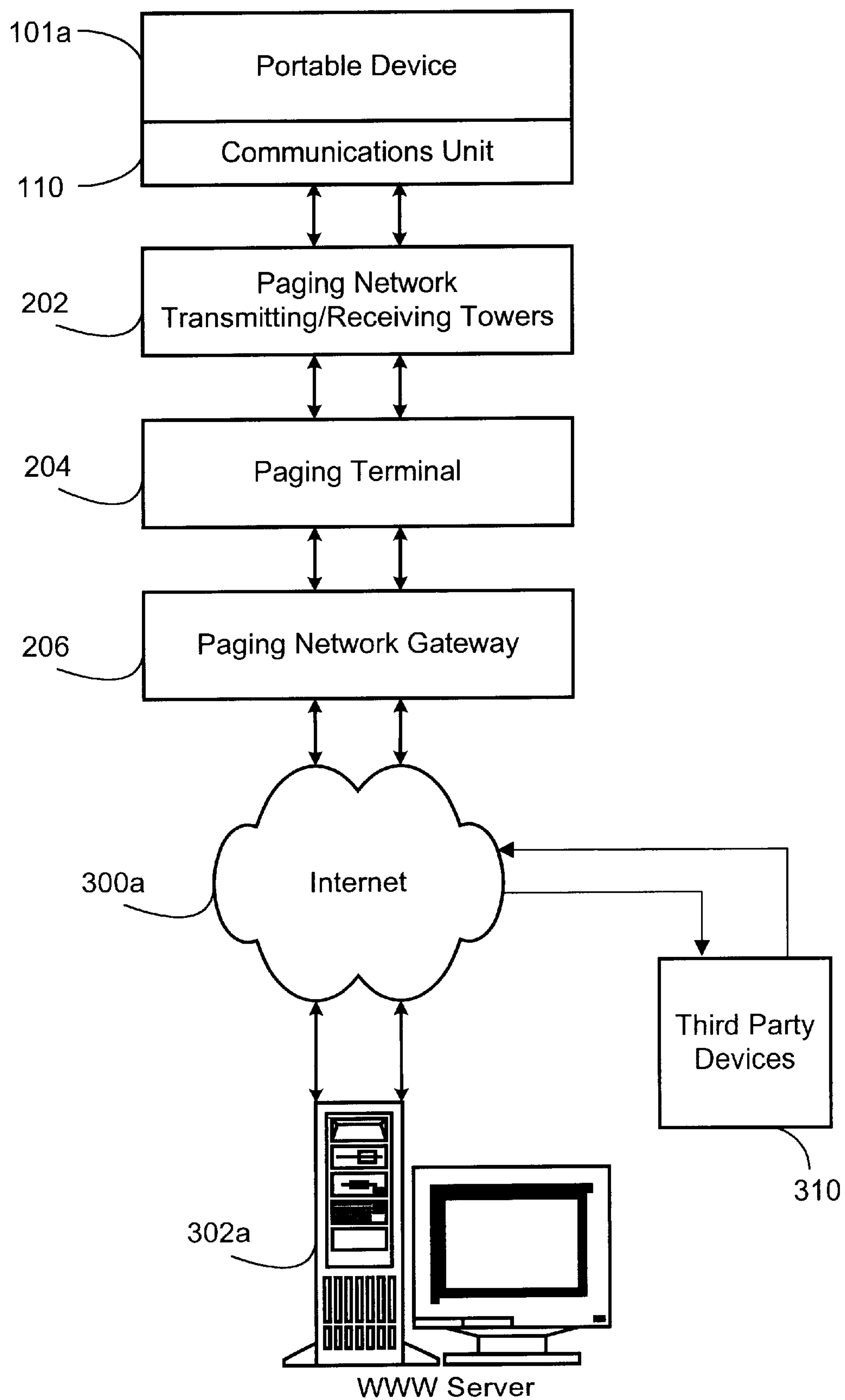
FIG. 5 is a diagram illustrating the signal path between a portable medical monitoring device and a server according to another embodiment.

FIG. 5 illustrates an embodiment with an at least partially wireless connection 200 between the portable device 101*a* and a remote computer, in this embodiment a WWW server 302*a*. Data is wirelessly transmitted from the portable device 101*a* by the communications unit 110 to a paging network receiving/transmitting tower 202. Packet-based paging protocols such as mobitex and reflex are well known in the art and are utilized in the preferred embodiments. Embodiments utilizing an alternative communications unit 110 such as mobile telephone communications utilize such protocols as GPRS, TDMA, or CDMA.

The data is transmitted to the paging network terminal 204, which directs the data to a paging network gateway 206 with an information network, such as the Internet 300*a*. The paging network gateway 206 forwards the data to the Internet 300*a*, for delivery to the web server 302*a*. An analogous process occurs in the reverse when statistical data is transmitted from the web server 302*a* to the communications unit 110 of the portable device 101*a*.

The web server 302*a* processes sensor and/or measurement data, or data related thereto (which is still referred to as sensor and/or measurement data) into statistical data. The server 302*a* utilizes sensor data or measurements associated with a specific physiological characteristic to calculate statistical data such an average value over time intervals, such as daily, weekly, or monthly intervals, and/or to calculate a variance, standard deviation, least square, or a distribution, for example. The remote computer 302 or web server 302*a* may also compute measurements from statistical data, etc. Such statistical data is transmitted from the server 302*a* through signal path 200 to the communications unit 110 of the portable device 101*a*. The electronic controller 102 directs storage and/or display of the statistical data.

The information stored in server 302*a* is available over the Internet to devices and computers 310 of a monitored person or health care professionals.

Figures 6C, 6D:
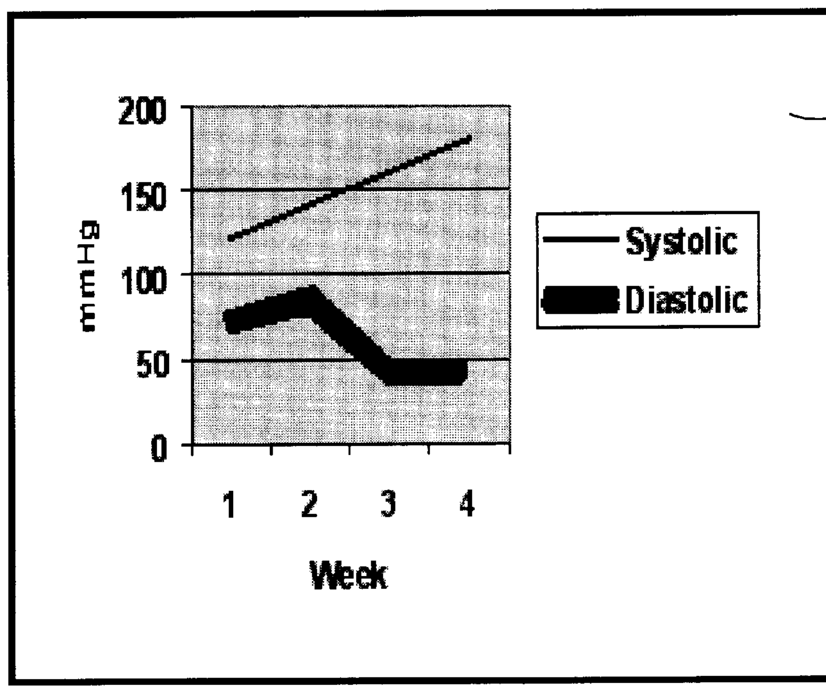

The display device 108 is a liquid crystal device (LCD). However, any suitable display device may be used. FIGS. 6*a*, 6*b*, and 6*c* illustrate statistical data displayed on the display device 108. Measurement data, statistical data, and sensor data can be displayed in any manner that effectuates a communication of the associated information to the monitored person. FIG. 6*d* is an example of statistical data displayed graphically. It is contemplated that statistical data, measurement data and sensor data can be graphically displayed alone or in combination and in any manner that effectuates communication of the associated information to the monitored person. Preferred graphical displays specifically include but are not limited to graphs, charts, and tables, such as histograms and other graphical communications of data.

Server 302*a* (FIG. 5) preferably includes automatic message alert functionality alerting the monitored person and authorized parties when sensor, measurement or statistical data is more than, less than, or equal to or is outside of a given range. The server 302*a* is programmed with at least one function, each function being associated with a specific physiological characteristic of a "generic" person, normative in relevant physiological respects. A value or range of values is produced when the function is considered in light of at least one parameter each associated with a specific physical trait of the particular monitored person, such as the person's age or weight. Such parameters are considered in order to tailor and/or personalize the function in a manner so as to yield a custom value or value range representative of medically satisfactory conditions for the associated physiological characteristic of the particular monitored person.

Once this value or value range has been ascertained, it is compared against either sensor data or statistical data. The choice of sensor, measured or statistical data more than, less than, equal to or is dependent on whether the particular function is associated with instantaneous thresholds or statistical thresholds. If the sensor measurement or statistical data is outside the value range, then the server transmits an automatic message alert indicative of an emergency medical condition associated with the specific monitored person whose data outside the value range.

Figure 7:
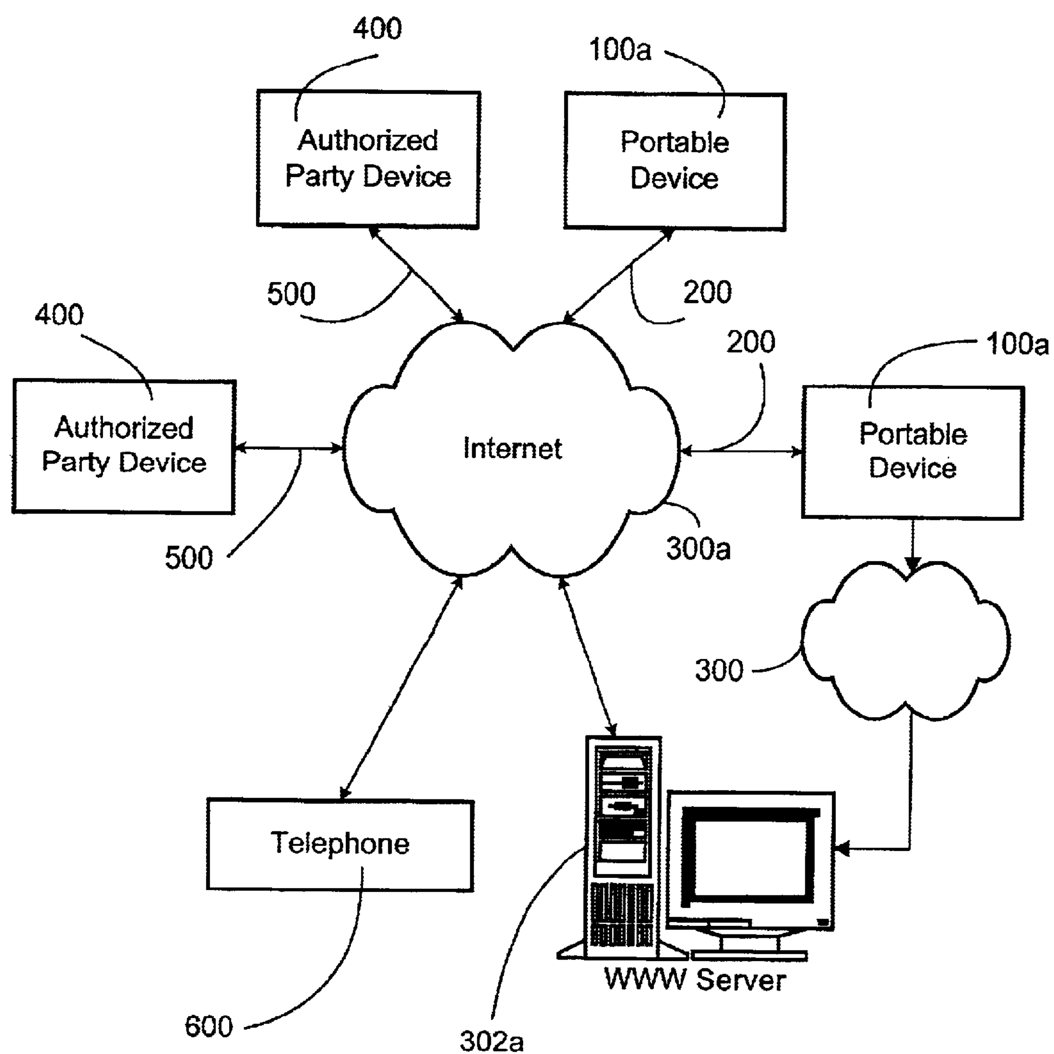
FIG. 7 is a diagram showing the communication signal path between a server, portable monitoring device, an authorized party device, and automated phone system.

FIG. 7 depicts a system 350 that includes portable devices 100*a* and authorized party devices 400 that communicate with a server 302*a*. Automatic message alerts are sent to the communications devices 400 of specified authorized parties, such as health care professionals and family members, as well as to the concerned portable device 100*a*. In this embodiment, the authorized party devices 400 may comprise a pager, telephone, mobile telephone, PC, or laptop computer. Both the portable device 100*a* and authorized party devices 400 are programmed to receive transmitted automated message alerts. In the preferred embodiments, there is any number and combination of authorized party devices 400. Methods of interconnectivity, signal paths 500, and data and protocol conversions between authorized devices 400 and the Internet 300 are varied and well known in the art, and often particular to the type of authorized party device 400 (i.e. mobile telephone, desktop computer, etc.). In the preferred embodiment, an automated message alert may be also initiated manually by the use of a touch tone telephone 600. Methods of interconnectivity, signal routing, and data and protocol conversion between the telephone 600, a telephone network (not shown), the Internet 300*a* and a communications network 300 are known in the art. Also, in the preferred embodiment, authorized party devices 400 also have access to the server 302*a* to view at least one of sensor data and statistical data. Access is subject to security measures such as password protection, and methods of security are well known in the art.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application. It is intended that the scope of the invention be defined by the claims appended hereto and their equivalents.

I claim:

1. A medical monitoring system comprising:

a plurality of portable electronics units each sized to be carried by a person being monitored and each comprising:

an electronic controller;

at least one memory coupled to the electronic controller that at least temporarily stores data provided by at least one sensor associated with the monitored person related to at least one physiological characteristic of the monitored person;

a communications unit coupled to the electronic controller that wirelessly transmits first data provided by or related to data provided by a first sensor and wirelessly receives statistical data including statistical data based on or related to first data transmitted by the communications unit and other statistical data not based on or related to first data transmitted by the communications unit, the statistical data received by the communications unit being stored at least temporarily in the at least one memory; and a display device that displays at least statistical data received by the communications unit; and the system including a remote computer and associated memory that at least temporarily stores first data transmitted by the communications unit and statistical data including statistical data based on or related to first data transmitted by the communications unit and other statistical data not based on or related to first transmitted by the communications unit, the communications unit of the electronics unit transmitting first data for receipt by a remote computer and receiving statistical data provided by a remote computer;

the display device displaying statistical data provided by a remote computer, including statistical data based on or related to first data transmitted by the communications unit and other statistical data not based on or related to first data transmitted by the communications unit.

2. The system of claim 1, wherein the communications unit comprises a two-way pager.

3. The system of claim 1, wherein the display device displays data provided by the at least one sensor stored in the at least one memory.

4. The system of claim 1, wherein the statistical data based on or relating to first data transmitted by the communications unit comprises at least one of an average, a variance, a standard deviation, a least square, a distribution, and a compilation of first data transmitted by the communications unit.

5. The system of claim 1, wherein the display device displays statistical data as at least one of text and graphics.

6. The system of claim 1, wherein the remote computer comprises a web server connected to the Internet.

7. The system of claim 1, comprising means for providing at least first data stored by the associated memory to authorized party devices in accordance with an authorization procedure.

8. The system of claim 1, wherein the controller is programmed to control transmission of first data by the communications unit for receipt by the remote computer in response to a user input to the electronics unit and to request statistical data from the remote computer in response to a user input to the electronics unit.

9. The system of claim 1, wherein the controller is programmed to control transmission of first data by the communications unit for receipt by the remote computer at programmed time intervals and to request statistical data from the remote computer at programmed time intervals.

10. The system of claim 1, wherein a remote computer is programmed to provide statistical data to an electronics unit according to programmed parameters.

* * * * *